US006743265B2

(12) United States Patent
Patel et al.

(10) Patent No.: US 6,743,265 B2
(45) Date of Patent: Jun. 1, 2004

(54) GRADUAL PERMANENT COLORING OF HAIR USING DYE INTERMEDIATES DISSOLVED IN ALKALINE WATER WITH A GELLING AGENT

(75) Inventors: Jitendra Patel, Fox River Grove, IL (US); Frank Jones, Schaumburg, IL (US)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 108 days.

(21) Appl. No.: 10/096,812

(22) Filed: Mar. 13, 2002

(65) Prior Publication Data

US 2003/0172468 A1 Sep. 18, 2003

(51) Int. Cl.$^7$ .................................................. A11K 7/13
(52) U.S. Cl. ........................ 8/405; 8/406; 8/408; 8/410; 8/411; 8/412; 8/421; 8/435; 8/540; 8/580; 8/581; 8/606; 8/611
(58) Field of Search ............................ 8/405, 406, 408, 8/410, 411, 412, 421, 435, 540, 580, 581, 606, 611

(56) References Cited

U.S. PATENT DOCUMENTS

| | | |
|---|---|---|
| 3,818,615 A | 6/1974 | Zeffren et al. |
| 3,912,446 A | 10/1975 | Zviak et al. |
| 3,931,912 A | 1/1976 | Hsiung |
| 4,096,243 A | 6/1978 | Feinland et al. |
| 4,104,021 A * | 8/1978 | Lapidus et al. ................ 8/10.2 |
| 4,297,098 A | 10/1981 | Dasher et al. |
| 4,369,037 A | 1/1983 | Matsunaga et al. |
| 4,402,700 A | 9/1983 | Feinland et al. |
| 4,566,876 A | 1/1986 | Brown et al. |
| 4,656,043 A | 4/1987 | Hawkins et al. |
| 4,749,565 A | 6/1988 | Grollier |
| 4,925,666 A | 5/1990 | Decker, Jr. et al. |
| 5,008,105 A | 4/1991 | Grollier et al. |
| 5,049,377 A | 9/1991 | Lamb et al. |
| 5,064,441 A | 11/1991 | Kawase et al. |
| 5,089,257 A | 2/1992 | Schrader et al. |
| 5,102,655 A | 4/1992 | Yoshihara et al. |
| 5,116,388 A | 5/1992 | Brooks |
| 5,130,124 A | 7/1992 | Merianos et al. |
| 5,221,286 A | 6/1993 | Singleton et al. |
| 5,376,146 A * | 12/1994 | Casperson et al. .............. 8/408 |
| 5,393,305 A | 2/1995 | Cohen et al. |
| 5,554,197 A * | 9/1996 | Assini et al. .................. 8/406 |
| 5,556,615 A | 9/1996 | Janchitraponvej et al. |
| 5,560,750 A | 10/1996 | Crews et al. |
| 5,730,966 A | 3/1998 | Torgerson et al. |
| 5,849,042 A | 12/1998 | Lim et al. |
| 5,942,216 A | 8/1999 | Herb et al. |
| 5,993,491 A | 11/1999 | Lim et al. |
| 6,022,381 A | 2/2000 | Dias et al. |
| 6,074,438 A | 6/2000 | Lim et al. |
| 6,143,286 A | 11/2000 | Bhambhani et al. |
| 6,309,426 B1 | 10/2001 | Dias et al. |
| 2003/0028979 A1 * | 2/2003 | Duffer et al. .................. 8/406 |

FOREIGN PATENT DOCUMENTS

| | | | |
|---|---|---|---|
| DE | 2 217 388 | 4/1972 | |
| DE | 100 51 774 | 4/2002 | |
| EP | 1 289 712 | * 9/1972 | ............. D06P/1/32 |
| EP | 0 146 350 | 12/1984 | |
| GB | 1 289 712 | 9/1972 | |
| WO | 00/10515 | 3/2000 | |
| WO | 01/76545 | 10/2001 | |

OTHER PUBLICATIONS

Derwent Abstract, XP 002236077 & JP 54 070442 A, Jun. 1, 1979.

* cited by examiner

Primary Examiner—Yogendra N. Gupta
Assistant Examiner—Eisa Elhilo
(74) Attorney, Agent, or Firm—Milton L. Honig

(57) ABSTRACT

A method for permanently dyeing hair which comprises subjecting said hair to a number of treatments, having a set time interval between each two consecutive such treatments, wherein each treatment comprises steps a.) and b.) below:

a.) contacting said hair, for a period of about 5 seconds to about 5 minutes with a recently made mixture of:
part ai: dye intermediates in water with a gelling agent at alkaline pH part aii an oxidizing compound such as hydrogen peroxide in water at acidic pH;

b.) rinsing said mixture from said hair with water;

and wherein said number of treatments is between about 2 to about 30; and wherein said set time interval between each two consecutive treatments is between about 8 hours and 30 days.

22 Claims, No Drawings

GRADUAL PERMANENT COLORING OF HAIR USING DYE INTERMEDIATES DISSOLVED IN ALKALINE WATER WITH A GELLING AGENT

BACKGROUND OF THE INVENTION

The present invention relates to a method for the permanent coloring of hair with minimized hair damage.

Most hair coloring products fall under three major groupings:

1. Temporary hair color.
2. Semi permanent hair color.
3. Permanent hair color.

Temporary hair color is a leave on product that causes minimal damage to the hair. However, temporary hair color causes stains, and leaches out under rain or with perspiration. Temporary hair color washes out with the next shampoo. Temporary hair color also does not give any control to the consumer over the amount of color deposited or the permanency of the color supplied. Temporary hair color does not result in a wide variety of colors and it has only a limited appeal.

Semi-permanent hair color comes as a rinse, and it causes minimal damage to the hair. However, semi-permanent hair color washes out to some degree with each shampoo and washes out completely within about 4 to 6 shampoos. Semi permanent hair color does not give the consumer any control regarding the amount of color deposited or the permanency of the color. Semi-permanent hair color has limited popularity with consumers.

Permanent hair color generally comes in two parts: a dye solution and a developer solution. Because of the damaging nature of conventional permanent dye or coloring treatments, most home coloring products come with a post treatment conditioner. In a permanent hair coloring treatment, the dye solution and the developer solution are mixed and then applied to the hair, which is then left for about 25 to about 35 minutes. The hair is then rinsed with water, treated with a post treatment conditioner, and then rinsed again with water.

Hair coloring products need to be applied every four to six weeks since hair grows out of the scalp at the rate of approximately one half inch per month. Each coloring application causes damage to the hair, and that damage is cumulative. Hair touch ups after the initial treatment may be needed, but these hair touch ups would also damage hair more, and so they may have to be avoided.

It would be desirable to develop a method for permanently coloring hair that minimizes the damage caused to hair by the coloring process. The present invention provides such a method.

Conventional hair coloring products cannot be used safely in the shower. It is an object of this invention to develop a method for permanently coloring hair, which can be carried out safely in the shower, for example. It is also an object of the invention to provide a method for permanently coloring hair wherein the user has control of the amount of durable color deposited without hair damage. It is also an object of the invention to provide a method for permanently coloring hair wherein the user can employ the hair coloring product as her daily or frequent hair care product to avoid new out growth of uncolored hair. It is also an object of the invention to provide a method for permanently coloring hair wherein said method involves less mess and difficulty than conventional permanent hair coloring methods. It is also an object of the invention to provide a method for permanently coloring hair wherein said method brings about gradual color changes with each application. Since gradual color changes are to occur, such a method would be virtually mistake free because the consumer could stop or alter the coloring method if she did not like the course the hair coloring was taking. It is also an object of the invention to provide a method for permanently coloring hair wherein the amount of hair coloring composition employed can be varied from application to application in order to adjust the hair coloring results.

These and other aspects of this invention will become evident by a detailed description of the invention given below.

Patents and patent applications related to the field of this invention are as follows:

U.S. Pat. No. 4,104,021 which discloses a process in which human hair is dyed in successive treatments at selected intervals with oxidation colors (aromatic primary amines and amino phenols) admixed in each treatment with an oxidizing agent ($H_2O_2$ or a derivative thereof)—the quantity of oxidation colorant applied in each treatment being substantially the same and the quantity of oxidizing agent being increased from the first to the last treatment to effect a gradual increase in depth of shade—the mixture being allowed to remain on the hair for substantially the same time in each treatment, followed by removal by rinsing.

U.S. Pat. No. 4,529,404 discloses an autoxidizable hair dye preparation capable of coloring or darkening hair when applied thereto and exposed to the atmosphere comprising a mixture of (I) at least one p-phenylene diamine compound, or An acid addition salt thereof, and (II) at least one 1,2,4-benzenetriol compound, each compound optionally containing nuclearly substituted $C_{1-4}$ alkyl, alkoxy, hydroxyalkyl or halogen. The preparation is preferably applied and exposed to the atmosphere repeatedly until the desired degree of darkening or color build-up is attained.

The preparations of this invention may also contain known additives or assistants such as hair grooming agents, for example quaternized vinyl pyrrolidone copolymers, carboxyvinyl polymers and the like, plasticizers, thickeners, slip and wetting agents such as polyoxyethylenated fatty (e.g. lauryl) alcohols, stearyldimethylammonium chloride, silicone copolymer, foam boosters, preservatives, perfumes and the like.

U.S. Pat. No. 5,968,486 describes a shampoo composition for lightening and highlighting hair which comprises (i) a peroxygen compound; and (ii) an anionic sulfonate;

said composition having a pH less than 5. There is also described an invention directed to a method for lightening and highlighting hair which comprises shampooing the hair with a lightening and highlighting effective amount of a composition of the invention.

U.S. Pat. No. 6,274,126 discloses a hair conditioning composition for conditioning, lightening, and highlighting hair, which comprises i) peroxygen compound, and ii) a conditioning agent, said composition having a pH of 5 or less.

U.S. Patent Application 2003/0051297 A1 discloses a method for permanently dyeing hair which comprises subjecting said hair to a number of treatments, having a set time interval between each two consecutive such treatments, wherein each treatment comprises steps a.) and b.) below:

a.) contacting said hair, for a period of about 5 seconds to about 5 minutes with a recently made mixture of:
i.) an alkaline composition comprising a dye intermediate in a shampoo base or in a conditioner base; and
ii.) an acidic composition comprising an oxidating compound in a shampoo base or in a conditioner base;
b.) rinsing said mixture from said hair with water;
with the proviso that when a conditioner base is present in a.) i.) above, an independently selected conditioner base is also present in a.) ii.) above; and when a shampoo base is present in a.) i.) above, an independently selected shampoo base is also present in a.) ii.) above;
and wherein said number of treatments is between about 2 to about 30; and wherein said set time interval between each two consecutive treatments is between about 8 hours and 30 days, is described.

SUMMARY OF THE INVENTION

The invention relates to a method for achieving permanent desired hair color change through the daily or frequent use of hair care compositions. The hair care compositions comprise a mixture of part ai and part aii as described just below:

Part ai: dye intermediates in water with gelling agent at alkaline pH;
Part aii: oxidizing compound in water at acidic pH.

DETAILED DESCRIPTION OF THE INVENTION

Unless otherwise indicated, all percentages used herein are percentages by weight of active material based on the weight of the respective composition.

When used herein % refers to weight % as compared to the total weight percent of the composition that is being discussed. For example, when % is used to discuss the amount of an ingredient that is in part ai, this means weight % as compared to the total weight of part ai. When weight % of the mixture of part ai and part aii is mentioned, this means the weight % as compared to the total weight the mixture of part ai and part aii. When the ratio of part ai to part aii is discussed this means the weight to weight ratio. As used herein the term "recently" means within a very short interval of time such as within a few seconds or minutes, such as within 0.01 seconds to 120 seconds, or within 0.1 seconds to 60 seconds, or within 0.5 second to within 30 seconds or within 2 seconds to within 20 seconds. As used herein "nearly simultaneously" means within about 0.001 second to about 5 seconds, more preferably about 0.01 to about 1 second, more preferably about 0.01 to about 0.5 second. As used herein "physical proximity" means within about 0.01 to about 1 cm, more preferably about 0.1 to about 0.5 cm. Compositions of the invention may be made by means which are known in the art or which are analogous to those which are known in the art. Ingredients which are included in compositions of the invention are known in the art or may be made by means which are known in the art.

Part ai can comprise from
a) about 0.1 to about 99.9% of aqueous base with a gelling agent;
b) about 0.1 to about 5% of dye intermediates or oxidation dyestuffs;
c) about 0.1 to about 5% of a coupling compound.

More preferably, part ai can comprise from
a) about 1 to about 99% of an aqueous base with a gelling agent;
b) about 0.1 to about 0.5% of oxidation dyestuffs;
c) about 0.1 to about 1% coupling compound.

Part aii can comprise from:
a) about 1 to about 99% of an aqueous base; and
b) about 1 to about 5% of an oxidizing compound.

Part aii more preferably comprises from:
c) about 2 to about 90% of an aqueous base; and
d) about 2 to about 5% of an oxidizing compound.

Aqueous compositions of the present invention can comprise a mixture of part ai and part aii wherein:

Part ai can comprise:
a) about 0.1% to about 99.9% of an aqueous base with gelling agent;
b) about 0.1% to about 1% of an oxidation dyestuff; and
c) a volatile silicone;

Part aii can comprise:
a) about 1 to about 90% of an aqueous base;
b) about 1 to about 5% of an oxidative compound.

One or both of part ai and part aii may further comprise a thickener which is a high molecular weight fatty alcohol wherein said high molecular weight fatty alcohol is selected from the group consisting of for example cetyl alcohol and stearyl alcohol.

Part ai and part aii can, for example, be mixed in a ratio of about 1.2:0.8 to about 0.8:1.2 respectively, more preferably at about a 1:1 ratio.

What follows is a description of the ingredients that can be included in the compositions of the present invention.

Hair Dyes and Hair Coloring Agents

The part ai compositions of the present invention include one or more oxidative hair coloring agents or oxidation dyestuffs. These hair coloring agents are present in compositions of the present invention which have an aqueous base. Such oxidative hair-coloring agents are used in combination with the oxidizing systems of the present invention to formulate permanent hair dye compositions.

Permanent hair dye compositions as defined herein are compositions, which once applied to the hair, are substantially resistant to washout.

Oxidative Dyes

The dye forming intermediates, also called dye intermediates or oxidation dyestuffs, used in oxidative dyes can be aromatic diamines, aminophenols and their derivatives. These dye forming intermediates can be classified as; primary and secondary intermediates, couplers and modifiers, and nitro dyes. Primary intermediates are chemical compounds, which by themselves will form a dye upon oxidation. The secondary intermediates, also known as color modifiers or couplers and are used with other intermediates for specific color effects or to stabilize the color. Nitro dyes are unique in that they are direct dyes, which do not require oxidation to dye the hair.

The oxidation dyestuffs or oxidation dye intermediates, which are suitable for, use in the compositions and processes herein include aromatic diamines, polyhydric phenols, aminophenols and derivatives of these aromatic compounds (e.g., N-substituted derivatives of the amines, and ethers of the phenols). Primary oxidation dye intermediates are generally colorless molecules prior to oxidation. The oxidation dye color is generated when the primary intermediate is 'activated' and subsequently enjoined with a secondary intermediate (coupling agent), which is also generally colorless, to form a colored, conjugated molecule. In general terms, oxidation hair dye precursors or intermediates include those monomeric materials which, on oxidation, form oligomers or polymers having extended conjugated systems of electrons in their molecular structure. Because of the new electronic structure, the resultant oligomers and polymers exhibit a shift in their electronic spectra to the visible range and appear colored. For example, oxidation dye precursors capable of forming colored polymers include materials such as aniline, which has a single functional group and which, on oxidation, forms a series of conjugated imines and quinoid dimers, trimers, etc. ranging in color from green to black. Compounds such as p-phenylenediamine, which has two functional groups, are capable of oxidative polymerization to yield higher molecular weight colored materials having extended conjugated electron systems. Color modifiers (couplers), such as those detailed hereinafter, are preferably used in conjunction with the oxidation dye precursors herein and are thought to interpose themselves in the colored polymers during their formation and to cause shifts in the electronic spectra thereof, thereby resulting in slight color changes. A representative list of oxidation dye precursors suitable for use herein is found in Sagarin, "Cosmetic Science and Technology", Interscience, Special Edition, Volume 2, pages 308 to 310 which is herein incorporated by reference.

It is to be understood that the oxidizing aids of the present invention are suitable for use (in combination with a source of peroxide as detailed herein) with all manner of oxidation dye precursors and color modifiers and that the precursors detailed below are only by way of example and are not intended to limit the compositions and processes herein.

The typical aromatic diamines, polyhydric phenols, aminophenols, and derivatives thereof, described above as primary dye precursors can also have additional substituents on the aromatic ring, e.g. halogen, aldehyde, carboxylic additional substituents on the amino nitrogen and on the phenolic oxygen, e.g. substituted and unsubstituted alkyl and aryl groups.

The hair coloring compositions of the present invention may, in addition to the essential oxidative hair-coloring agents, optionally include non-oxidative and other dye materials. Optional non-oxidative and other dyes suitable for use in the hair coloring compositions and processes according to the present invention include semi-permanent, temporary and other dyes. Non-oxidative dyes as defined herein include the so-called 'direct action dyes', metallic dyes, metal chelate dyes, fiber reactive dyes and other synthetic and natural 'Chemical and Physical Behaviour of Human Hair' 3rd Edn. by Clarence Robbins (pp 250–259); 'The Chemistry and Manufacture of Cosmetics'. Volume IV. 2nd Edn. Maison G. De dyes. Various types of non-oxidative dyes are detailed in: 'Navarre' at chapter 45 by G. S. Kass (pp 841–920); 'cosmetics: Science and Technology' 2nd Edn, Vol II Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139).

Specific hair dyes which may be included in the compositions of the invention include m-aminophenol, p-phenylene diamine, p-toluenediamine; p-phenylenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-N,N-bis-(2-hydroxyethyl)-N,N-bis(4-aminophenyl)-2-propanol; 2-methyl-4-dimethylaminoaniline; p-aminophenol; p-methylaminophenol; 3-methyl-p-aminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol; 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol(2-isopropyl-5-methylphenol); 1,5-dihydroxy-1,2,3,4-tetrahydronaphthalene; 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole; bis(2,4-diaminophenoxy)-1,3-propane; 1-hydroxyethyl-2,4-diaminobenzene; 2-amino-4 hydroxyethylaminoanisole; aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis(hydroxyethylamino)toluene; m-aminophenol; 2-hydroxy-4-carbamoylmethylaminotoluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylpheno; 2-dimethylamino-5-aminopyridine; 2,4,5,6-tetra-aminopyrimidine; 4,5-diamino-1-methylpyrazole; 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethoxy-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, or combinations thereof.

Buffering Agents

The final coloring compositions of the present invention (that is after part ai and part aii have been mixed) have a preferred pH in the range of from about 7 to about 12, more preferably from about 8 to about 10.

Buffering agents may be present in part ai and part aii compositions of the present invention. Coloring compositions of the present invention may contain one or more hair swelling agents (HSAs) such as urea, to adjust the pH to the desired level. Several different pH modifiers can be used to adjust the pH of the final composition or any constituent part thereof.

Further examples of suitable buffering agents are ammonium hydroxide, urea, ethylamine, dipropylamine, triethylamine and alkanediamines such as 1,3-diaminopropane, anhydrous alkaline alkanolamines such as, mono or di-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-alginine, lysine, oxylysine and histidine and alkanolamines such as dimethylaminoethanol and aminoalkylpropanediol and mixtures thereof. Also suitable for use herein are compounds that form $HCO_3$—by dissociation in water (hereinafter referred to as 'ion forming compounds'). Examples of suitable ion forming compounds are $Na_2CO_3$, $NaHCO_3$, $K_2CO_3$, $(NH_4)_2CO_3$, $NH_4HCO_3$, $CaCO_3$ and $Ca(HCO_3)_2$ and mixtures thereof.

As herein before described certain alkaline buffering agents such as ammonium hydroxide and monoethylamine (MEA), urea and the like can also act as hair swelling agents (HSA's).

Preferred for use as a buffering agent for the coloring compositions according to the present invention is ammonium hydroxide and/or sodium hydroxide.

In oxidizing and coloring kits comprising a portion of peroxide oxidizing agent, which may be present in either solid or liquid form, such as hydrogen peroxide, a buffering agent solution is required to stabilize hydrogen peroxide. Since hydrogen peroxide is stable in the pH range from 2 to 4, it is necessary to use a buffering agent having a pH within this range. Dilute acids are suitable hydrogen peroxide buffering agents. Phosphoric acid is a preferred agent for buffering hydrogen peroxide solutions.

This pH adjustment can be effected by using well known acidifying agents in the field of treating keratinous fibers, and in particular human hair, such as inorganic and organic acids such as hydrochloric acid, tartaric acid, citric acid, and carboxylic or sulphonic acids such as ascorbic acid, acetic acid, lactic acid, sulphuric acid, formic acid, ammonium sulphate and sodium dihydrogenphosphate/phosphoric acid, disodium hydrogen phosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid and mixtures thereof.

Solvents

Water is the preferred principal diluent or solvent for the compositions according to the present invention. As such, the compositions according to the present invention may include one or more solvents as additional diluent materials. Generally, the solvent is selected to be miscible with water and innocuous to the skin. Solvents suitable for use herein include $C_1$–$C_{20}$ mono- or polyhydric alcohols and their ethers, glycerine, with monohydric and dihydric alcohols and their ethers preferred. In these compounds, alcoholic residues containing 2 to 10 carbon atoms are preferred.

Thus, a particularly preferred group includes ethanol, isopropanol, n-propanol, butanol, propylene glycol, ethylene glycol monoethyl ether, and mixtures thereof.

These solvents may be present in part ai and part aii of the invention.

Thickeners of Gelling Agents

Thickeners may be included in part ai and part aii of the invention. Long chain fatty alcohols having from about 11 to about 18 carbon atoms in the long fatty chain can be thickener constituents of compositions of this invention. These alcohols can be used alone, or in admixture with each other. When included in the compositions, the alcohol is preferably present at from about 0.5 to about 10 weight percent of the composition, and more preferably at from about 2 to about 5 weight percent.

Lauryl alcohol, oleyl alcohol, myristyl alcohol, stearyl alcohol, and the like, and mixtures thereof are contemplated herein. In addition, mixtures of natural or synthetic fatty alcohols having fatty chain lengths of from about 11 to about 18 carbons are also useful. Several such mixtures are available commercially, and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals.

Thickening agents suitable for use in the compositions herein may also be selected from oleic acid, cetyl alcohol, oleyl alcohol, sodium chloride, cetearyl alcohol, stearyl alcohol, synthetic thickeners such as Carbopol, Aculyn and Acrosyl and mixtures thereof. Preferred thickeners for use herein are Aculyn 22 (RTM), steareth-20 methacrylate copolymer; Aculyn 44 (RTM) polyurethane resin and Acusol 830 (RTM), acrylates copolymer that are available from Rohm and Haas, Philadelphia, Pa., USA. Additional thickening agents suitable for use herein include sodium alginate or gum arabic, or cellulose derivatives, such as methyl cellulose or the sodium salt of carboxymethylcellulose or acrylic polymers.

Fatty alcohols of the above discussed carbon chain lengths which are ethoxylated to contain an average of one or two moles of ethylene oxide per mole of fatty alcohol can be used in place of the fatty alcohols themselves. Examples of such useful ethoxylated fatty acids include ethylene glycol cetyl ether, polyoxyethylene (2) stearyl ether, and the like; the exemplary compounds having CTFA Dictionary names of Ceteth-1 and Steareth-2, respectively.

Volatile Silicones

Volatile silicones may also be employed in the compositions of the invention. The volatile silicone oil is often described as a volatile polyorganosiloxane, and is a liquid material having a measurable vapour pressure at ambient conditions (about 20 to 25° C.). Typically the vapour pressure of volatile silicones lies in the range of from 1 or 10 Pa to 2 kPa at 25° C. Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $1 \times 10^{-5}$ m2/sec (10 centistokes), and particularly above $1 \times 10^{-7}$ m2/sec (0.1 centistokes), the linear siloxanes normally exhibiting a viscosity of below $5 \times 10^{-6}$ m2/sec (5 centistokes).

The volatile silicones can also comprise branched linear or cyclic siloxanes such as the aforementioned linear or cyclic siloxanes substituted by one or more pendant —O—Si(CH3)3 groups. Examples of commercially available silicone oils include oils having grade designations 344, 345, 244, 245 and 246, (from Dow Corning Corporation) Silicone 7207 and Silicone 7158 (from Union Carbide Corporation) and SF1202 (from General Electric [US]).

The non-volatile oil can comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series having a viscosity of at least 50 centistokes.

Non-Volatile Silcones

Non-volatile silicones may be included in compositions of the invention. Nonvolatile silicone oils include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile silicones useful in the present compositions are the polydimethyl siloxanes having viscosities from about 10 to about 400 centistokes at 25° C.

Optional Ingredients

The compositions of the present invention can comprise a wide range of optional ingredients. The ingredients can fall into the following functional classes: anticaking agents, antioxidants, binders, biological additives, bulking agents, chelating agents, chemical additives, colorants, cosmetic astringents, cosmetic biocides, denaturants, drug astringents, emulsifiers, film formers, fragrance components, humectants, opacifying agents, plasticizers, preservatives, propellants, reducing agents, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and the like.

Other optional ingredients include organic acids. A non-exclusive list of examples of organic acids which can be used as the proton donating agent are adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof. Non-exclusive lists of examples of mineral acid for use herein are hydrochloric, phosphoric, sulfuric and mixtures thereof.

It has been found by experimentation that hair care products used on a daily or frequent basis can achieve durable desired hair color. As noted above, the daily hair care product consists of two parts.

Part ai: dye intermediates in water with a gelling agent at alkaline pH

Part aii: an oxidizing compound such as hydrogen peroxide in water at acidic pH.

Part ai is mixed with part aii and applied to hair. The reason conventional hair coloring products come in two packages is because the mixture of the coloring component and the oxidizing component is unstable and the two components must be kept apart until just before use. Similarly part ai and part aii of the present invention must be kept apart until just before use. By varying the concentration of the actives and the treatment time, the amount of color on hair could be varied while minimizing hair damage. To make the product more convenient and fool proof, part ai and aii can be packaged in dual dispensing systems where both parts are mixed out side of the package when dispensed which is then applied to the wet hair as a hair colorant. Depending upon the amount of color desired, the treatment time could be varied from one or two minutes or longer.

Such treatments would add color to hair gradually without damage due to lower contact time. Each subsequent treatment would add color until the desired shade is obtained. Depending upon the concentration of the actives and contact time, a desired shade may be reached in about six to eight treatments. It has been found that since any one treatment does not exceed the threshold of irreversible damage, the total damage resulting from multiple treatments is lower than the damage from a single conventional treatment. Such a process gives the user control over the amount of color deposited on her hair, and also the option to discontinue further applications if the color delivered is not to her liking. She also has the option to switch to another color shade immediately without having to wait the six to eight weeks that is recommended for conventional treatments. With conventional hair color treatment, it is not recommended to perm and color hair simultaneously due to extensive damage. However, since the method of the invention colors the hair with minimum damage, perming can be done in the same time frame with this progressive coloring treatment.

The following examples, which were made by means that are conventional in the art, are shown as illustrations only and are not intended to limit the scope of the invention:

FORMULA #1

| Dark Brown Color: Part ai | % |
| --- | --- |
| Carbopol 940 | 1.0 |
| Disodium EDTA | 0.10 |
| DC-1870 HV | 1.80 |
| Kathon CG 1.5% | 0.08 |
| DMDM Hydantoin 55% | 0.10 |
| Fragrance | 0.20 |
| Sodium metabisulfite | 0.10 |
| m-Aminophenol | 0.03 |
| Rodol Gray HED | 0.13 |
| p-Phenylenediamine | 0.45 |
| o-Aminophenol | 0.05 |
| Resorcinol | 0.25 |
| Sodium hydroxide 50% | 0.40 |
| DI Water | to 100.00 |

PH = 8 to 9

| Dark Brown Color: Part aii | |
| --- | --- |
| Polymer JR-30M | 0.5 |
| Disodium EDTA | 0.10 |
| DC-1870 HV | 1.80 |
| Hydrogen Peroxide (35%) | 10.00 |
| DMDM Hydantoin 55% | 0.10 |
| Fragrance | 0.20 |
| Phosphoric acid, 85% | 0.09 |
| DI Water | to 100.00 |

PH = 3.0

Take equal amounts of part ai and part aii (formula#1), mix and apply to the wet hair tresses, keep on hair tresses for two minutes, and rinse well. Repeat the above procedure for subsequent treatments. Collect the hair tress after 2, 4 and 6 treatments. Measure the change in color delta E using McBeth Coloreye. Similarly take equal amounts of part ai and aii (formula#1), mix and apply to the wet hair tresses, keep on hair tresses for 30 mins, and rinse well. Measure the change in color delta E using McBeth ColorEye.

Difference of color as compared against untreated hair, $\Delta E$ is: $\sqrt{(\Delta L^2 + \Delta a^2 + \Delta b^2)}$ Conventional Formula #2

L'Oreal Dark Brown Permanent Hair Color

Color the hair tresses using L'Oreal dark brown permanent hair color. Follow the instruction sheet. Measure the change in color delta E using McBeth coloreye.

The changes in delta E values are summarized in the table below. One can see from the results that the change in color after one 30-min. treatment with L'Oreal Dark Brown is very similar to one 30 mins and six 2-min. treatment using a composition of the invention. The good correlation was observed with number of treatments and change in the color of the hair. It takes about six treatments to achieve a single 30 minutes treatment of permanent conventional color.

|  | L'Oreal's Preference: Dark Brown: Delta E | Invention: Dark Brown Color Delta E |
| --- | --- | --- |
| 1X-30 mins. | 4.28 | 4.35 |
| 2X-2 mins. |  | 1.78 |
| 4X-2 mins. |  | 3.55 |
| 6X-2 mins. |  | 4.12 |

Treatment of hair with compositions of the invention as described herein gives said hair good attributes such as lower wet combing force, higher break stress, lower amounts of cysteic acid (which are an indicator of hair damage), good hair color change, less color fading, less damage to hair, and more intense color to hair as described just below. Also described below is a method for applying compositions of the invention at set time intervals so as to avoid root outgrowth and less color fading Combing Index—

The combing experiment has been carried out to evaluate the extent of damage. Wet combing evaluation technique has been used to correlate damage. The combing index was measured to evaluate the extent of damage. Higher index (more than one) indicates lower damage.

Combing Index=Combing force of untreated hair/combing force of treated with composition of the invention.

The above tresses were evaluated via Instron to measure combing force.

| Treatments | Combing force gm force |
| --- | --- |
| Untreated hair | 27.15 |
| Treated with color gel | 16.25 |

Combing Index=Combing force of untreated hair/combing force of treated with composition of the invention.
=27.15/16.25
=1.67

Wet Combing Force:

After conventional hair color treatment, it is hard to comb the hair. Harder combing indicates more hair damage. The combing force was measured using Instron.

The combing force with new conditioner composition of the invention is in the range of 5 to 55 gm force, preferably 5 to 25 and more preferably 5 to 18 gm force.

Break Stress:

After conventional hair color treatment, the hair becomes weak and easy to break. The weak hair is again a sign of damage. The strength of the hair was measured using Instron.

The break stress with new conditioner composition of the invention is in the range of 0.005 to 0.03 gm force/micron, preferably 0.005 to 0.025 and more preferably 0.005 to 0.018 gm force/micron.

Cysteic Acid:

Much of the hair damage associated with conventional hair color treatment comes from the oxidation of cystine residues to the corresponding cysteic acid, with a consequent decrease in the tensile strength of hair as these cross-linkages are destroyed. A good measure of oxidative damage is thus the amount of cysteic acid formed in hair. Infrared transmission spectroscopy has been used to determine cysteic acid content in hair. The ratio of absorption at 1040 cm–1/absorption at 1240 cm–1 would indicate the extent of damage. A lower ratio indicates less hair damage.

The ratio of 1040/1240 with new color compositions of the invention is in the range of 0.01 to 1.5, preferably 0.01 to 1.0, and more preferably 0.01 to 0.5.

Hair damage done by hair coloring compositions can be calculated according to the following mathematical formulas:

% Damage=Chemical damage×Physical damage

% Damage=amount of cysteic acid×combing force gm×breaking stress force gm/micron 2×100

% Damage using L'Oreal's conventional preference permanent hair color for example $= 0.75 \times 48 \times 0.02 \times 100$ $= 72\%$ damage % Damage using new hair color composition of the invention:

0.25×20×0.015×100=7.5% damage

The above numbers indicate that the hair color compositions of the invention damage hair much less than conventional permanent hair color.

Color Change/Color Control:

The conventional permanent hair color system gives the color change delta E of 5 to 65 on blonde hair, and color change up to delta E of 1 to 8 on brown hair with one treatment. In conventional hair coloring treatments, consumers have little or no control of color, control of hue and control of lightening. By contrast, by using the gradual stepwise methods of the invention, the consumer has a great deal of control over hair color.

With the composition and method of the invention, there can be can delivered delta E of 0.1 to 65 on blonde hair and delta E of 0.1 to 8 on brown hair.

Root Outgrowth:

Conventional permanent hair color systems are used once in 4 to 6 weeks. During this time due to the new hair growth, roots look totally different than rest of the hair. On average the hair grow 1 cm/month or 0.3 mm/day.

With the present compositions and methods of the invention, used as a conditioner one would add color on each application of said compositions. Laboratory evaluation indicates that one would add 10% of the color change per conditioning treatment.

The amount of color added is determined by the following mathematical formulas.

The length of the new hair=0.3 mm×no. of days.

$$\% \text{ color added to new hair (10 days)} = \text{No of days} \times \% \text{ color added per day}$$
$$= 10 \times 10\%$$
$$= 100\% \text{ color}$$

Due to the constant addition of the color 10% per day, one will not be able to see root outgrowth.

Color Fading:

The conventional permanent hair color system is used once in 4 to 6 weeks. During this time color fades with washing, and outside exposure due to the weathering effect. The amount of color fading will depend upon washing and outside exposure. Let us assume that person wash his/her hair 4 times a week and stay outdoors for 2.0 hrs a day. The percentage of the color loss can be calculated using following equation.

Laboratory evaluation indicates that one would lose 1% of the color per wash and would loose about 0.75% of the color/hr of outside exposure.

$$\% \text{ Loss of color} = \text{no. of washing} \times \% \text{ color loss/wash} + \text{no of hrs. of exposure} \times \% \text{ color loss}/hr$$

$$\% \text{ Loss of color per month} = 20 \times 1.0 + 40 \text{ hrs} \times 0.75$$
$$= 20 + 30$$
$$= 50\%$$

$$\% \text{ Loss of color per week} = 12.5\%$$

So, on average consumer would lose 50% of the color. That is why most consumers want to recolor their hair every 4 to 6 weeks.

With the present composition and methods, one would add color on each application of composition, according to the schedule set forth by the following mathematical formulas.

$$\% \text{ Color addition/week} = \text{no of conditioning treatment week} \times \text{amount color added/treatment}$$

Laboratory evaluation indicates that one would add 6% more color per conditioning treatment.

$$\% \text{ Color addition/week} = 3 \times 10\% = 30\%$$

With a composition of the invention, one would lose 12.5% of the color but one would add 30% of the color. Due to this, one would not see any fading of the color and color would stay fresh everyday.

More Intense Color:

The typical permanent color composition, upon application goes through an oxidation mechanism. Each of the dye intermediates can produce pigments through oxidation and polymerization. According to Le Chatelier's principle, the state of a chemical reaction is a dynamic state in which the chemical reaction is occurring in both directions. The rate of reaction depends upon the ratio of the rate of forward reaction to the rate of backward reaction. The higher the ratio the faster is the reaction. The factors affecting the rate of reactions are as follows:

1. Reactants
2. Products
3. Pressure
4. Temperature

A main difference in the reaction using a conventional permanent color system is the temperature. With the conventional system, the reaction takes place at room temperature, at about 70–75 F.F., while with new system of the invention, since it is used in the shower, the reaction takes place at higher temperatures of about 100 to 110 F. According to le Chatelier's principle, the effect of temperature is very significant to the final rate of reaction.

Under identical conditions, laboratory evaluation indicates that one would increase 5% intensity of the color with 10F.-temperature difference.

Therefore, according to the mathematical formula just below, 15% more color is added using the compositions and methods of the invention as opposed to conventional hair coloring methods.

$$\% \text{ Additional Color} = \text{delta } T \times \% \text{ change in color per one degree F difference}$$
$$= (100 F - 70F) \times 0.5$$
$$= 30 \times 0.5 = 15\% \text{ more color due to new method}$$

If the contact time is kept at about two minutes or below for each treatment with compositions of the invention then there is no appreciable hair damage no matter how many color application treatments according to the invention are performed.

At the same time that hair damage is avoided by the methods of the invention, the consumer's hair is gradually being brought to the desired shade and color. This gradual change of color has two advantages: first, since the color is changed gradually, the consumer can stop the process if she does not like the color her hair is turning to. Second, some consumers do not want an abrupt change in color because they may feel embarrassed in public after having made such an abrupt change to the color of their hair. Moreover, the method and compositions of the present invention can be used in the shower, and on a frequent or daily basis, because the compositions and methods of the present invention, by contrast with conventional color compositions, do not employ poisonous levels of chemicals and also because compositions methods of the present invention involve hair application steps that are up to about two minutes in length. By contrast conventional hair coloring compositions require approximately 30 minutes' time for each application, an amount of time, which is clearly not suitable for use in the shower.

The methods of the present invention are not as messy as conventional permanent hair coloring methods. The methods of the present invention do not use chemical compositions that are as smelly and noxious as those used in conventional permanent hair-coloring methods. Because the methods of the invention can be carried out in the shower, they do not involve the dripping and the mess associated with conventional permanent hair coloring, which is usually done over the bathroom sink. The methods of the present invention do not use chemical compositions that can stain fixtures in the bathroom or that will stain the scalp and the face.

A dual package which can be employed in the products and kits of the present invention is disclosed in U.S. Pat. No. 6,082,588 to Markey et al which is hereby incorporated by reference.

Kit Containing an Instruction Sheet

The invention also relates to a kit for carrying out the hair coloring method of the invention. The kit comprises part ai, part aii and a post treatment solution, each in a separate container or in a dual container, as described herein. The kit also contains written instructions that explain how the compositions of the invention are used.

The consumer admixes the components of the kit according to written instructions, to obtain the aqueous reaction mixture. The mixing may be conducted in a separate vessel external to the kit, or may take place in a container of the kit adapted to provide sufficient head space for mixing. The components that are mixed are part ai and part aii. Part ai and part aii may also be admixed on the hair of the user. Essentially upon mixing, reaction of part ai and part aii will commence. After treatment for a desired time the mixture of part ai and part aii may be removed, preferably with water or a conventional shampoo or a conventional conditioning shampoo.

As noted above, dye intermediate composition and peroxygen composition are mixed together, and the resulting mixture may be applied to the hair and allowed to remain for a set time, usually about 1 to about 2 minutes; or about 1 hour or to about 30 minutes; or about 40 minutes.

Desired change in hair color by the method of the invention is described by the mathematical formulas described above. Monitoring desired change in hair color can be done in a number of ways. In the first instance, the consumer can compare her hair color with desired hair color or the hair color of a sample tress. Hair dyeing by the method of the invention can be repeated until her hair color matches the desired hair color. It is noted that the compositions used in the methods of the invention have lower contact times and thus repeated use of these compositions will not cause hair damage. An unexpected discovery of the present invention is that for damage to hair to occur, contact time in each treatment must go above the threshold value of about two minutes. Thus, the consumer can lighten or color the hair through repeated applications wherein the duration of each color application is about two minutes or less. The following two advantages are thereby achieved: first, there is a stepwise approach to the desired color; and second, a minimum of hair damage is done.

By the method of the invention, durable desired hair color, with a minimum of hair damage is achieved.

In following the method of the invention, the consumer can compare the color of her hair with the desired hair color, which can be printed on the package of the product. The consumer can also vary the number of days of application of the product, and the consumer can also vary the amount of time the mixture of part ai and part aii is left in the hair on each application. The number of applications can vary from about 7 to about 30 applications. The time of each application can vary from about 1 to about two minutes.

The method of the invention occurs over the course of days. Therefore, the final color of the consumer's hair may be affected by the amount of exposure to the sun of the hair during the course of treatment.

Desired hair color can also be reached by comparing hair after each treatment until it matches hair tresses taken from the consumer during a prior treatment.

Desired hair color can also be reached by testing the hair after each treatment with instruments, which measure the color of the hair. When the measurements of hair color of the treated hair reach a desired level, the treatment hair reach a desired level, the treatment can be stopped.

Indeed, reaching the desired hair color can be achieved by the use of any matching or comparison method commonly employed in the art.

Obviously, many modifications and variations of the invention as hereinbefore set forth can be made without departing from the spirit and scope thereof.

What is claimed is:

1. A method for permanently dyeing hair which comprises subjecting said hair to a number of treatments, having a set time interval between each two consecutive such treatments, wherein each treatment comprises:

a.) contacting said hair for a period of about 5 seconds to about 3 minutes with a recently made mixture of:
   part ai: dye intermediates in water with a gelling agent at alkaline pH, and
   part aii: oxidizing compound in water at acidic pH;

b.) rinsing said mixture from said hair with water;

and wherein said number of treatments with an identically formulated mixture is at least 6; and wherein said set time interval between each two consecutive treatments is between about 8 hours and 30 days.

2. A method according to claim 1, wherein said dye intermediate is selected from the group consisting of:

m-aminophenol,
p-phenylene diamine,
p-toluenediamine;
2-chloro-p-phenylenediamine;
N-phenyl-p-phenylenediamine;
N-2-methoxyethyl-p-phenylenediamine;
N,N-bis-(hydroxyethyl)-p-phenylenediamine;
2-hydroxymethyl-p-phenylenediamine;
2-hydroxyethyl-p-phenylenediamine;
4,4'-diaminodiphenylamine;
2,6-dimethyl-p-phenylenediamine;
2-isopropyl-p-phenylenediamine;
N-(2-hydroxypropyl)-p-phenylenediamine;
2-propyl-p-phenylenediamine;
1,3-N,N-bis-(2-hydroxyethyl)-N,N-bis(4-aminophenyl)-2-propanol;
2-methyl-4-dimethylaminoaniline;
p-aminophenol;
p-methylaminophenol;
3-methyl-p-aminophenol;
2-hydroxymethyl-p-aminophenol;
2-methyl-p-aminophenol;
2-(2-hydroxyethylaminomethyl)-p-aminophenol;
2-methoxymethyl-p-aminophenol;
5-aminosalicylic acid;
catechol;
pyrogallol;
o-aminophenol;
2,4-diaminophenol;
2,4,5-trihydroxytoluene;
1,2,4-trihydroxybenzene;
2-ethylamino-p-cresol;
2,3-dihydroxynaphthalene;
5-methyl-o-aminophenol;
6-methyl-o-aminophenol;
2-amino-5-acetaminophenol;
2-methyl-1-naphthol;
1-acetoxy-2-methylnaphthalene;
1,7-dihydroxynaphthalene;

resorcinol;
4-chlororesorcinol;
1-naphthol;
1,5-dihydroxynaphthalene;
2,7-dihydroxynaphthalene;
2-methylresorcinol;
1-hydroxy-6-aminonaphthalene-3-sulfonic acid;
thymol (2-isopropyl-5-methylphenol);
1,5-dihydroxy-1,2,3,4-tetrahydronaphthalene;
2-chlororesorcinol;
2,3-dihydroxy-1,4-naphthoquinone;
1-naphthol-4-sulfonic acid;
m-phenylenediamine;
2-(2,4-diaminophenoxy)ethanol;
N,N-bis(hydroxyethyl)-m-phenylenediamine;
2,6-diaminotoluene;
N,N-bis(hydroxyethyl)-2,4-diaminophenetole;
bis(2,4-diaminophenoxy)-1,3-propane;
1-hydroxyethyl-2,4-diaminobenzene;
2-amino-4 hydroxyethylaminoanisole;
aminoethoxy-2,4-diaminobenzene;
2,4-diaminophenoxyacetic acid;
4,6-bis(hydroxyethoxy)-m-phenylenediamine;
2,4-diamino-5-methylphenetole;
2,4-diamino-5-hydroxyethoxytoluene;
2,4-dimethoxy 1,3-diaminobenzene;
2,6-bis(hydroxyethylamino)toluene;
2-hydroxy-4-carbamoylmethylaminotoluene;
m-carbamoylmethylaminophenol;
6-hydroxybenzomorpholine;
2-hydroxy-4-aminotoluene;
2-hydroxy-4-hydroxyethylaminotoluene;
4,6-dichloro-m-aminophenol;
2-methyl-m-aminophenol;
2-chloro-6-methyl-m-aminophenol;
2-hydroxyethoxy-5-aminophenol;
2-chloro-5-trifluoroethylaminophenol;
4-chloro-6-methyl-m-aminophenol;
N-cyclopentyl-3-aminophenol;
N-hydroxyethyl-4-methoxy-2-methyl-m-aminophenol;
5-amino-4-methoxy-2-methylpheno;
2-dimethylamino-5-aminopyridine;
2,4,5,6-tetra-aminopyrimidine;
4,5-diamino-1-methylpyrazole;
1-phenyl-3-methyl-5-pyrazolone;
6-methoxy-8-aminoquinoline;
2,6-dihydroxy-4-methylpyridine;
5-hydroxy-1,4-benzodioxane;
3,4-methylenedioxyphenol;
4-hydroxyethylamino-1,2-methylenedioxybenzene;
2,6-dihydroxy-3,4-dimethylpyridine;
5-chloro-2,3-dihydroxypyridine;
3,5-diamino-2,6-dimethoxypyridine;
2-hydroxyethylamino-6-methoxy-3-aminopyridine;
3,4-methylenedioxyaniline;
2,6-bis-hydroxyethoxy-3,5-diaminopyridine;
4-hydroxyindole;
3-amino-5-hydroxy-2,6-dimethoxypyridine;
5,6-dihydroxyindole;
7-hydroxyindole;
5-hydroxyindole;
2-bromo-4,5-methylenedioxyphenol;
6-hydroxyindole;
3-amino-2-methylamino-6-methoxypyridine;
2-amino-3-hydroxypyridine;
2,6-diaminopyridine;
5-(3,5-diamino-2-pyridyloxy)-1,3-dihydroxypentane;
3-(3,5-diamino-2-pyridyloxy)-2-hydroxypropanol;
4-hydroxy-2,5,6-triaminopyrimidine,
or combinations thereof.

3. A method according to claim 1, wherein part ai, prior to mixture with part aii, has a pH of about 8 to about 10.

4. A method according to claim 1, wherein part aii, prior to mixture with part ai, has a pH of about 3 to about 5.

5. A method according to claim 1 wherein part ai comprises:
   A.) from about 0.05% to about 1.0% of a dye intermediate;
   B.) from about 0.1% to about 0.5% of a coupler; and
   C.) from about 1% to about 99% of an aqueous base.

6. A method according to claim 1 wherein part aii comprises:
   A.) from about 1% to about 99% of an aqueous base;
   B.) from about 0.5% to about 2.5% of a volatile silicone; and
   C.) from about 0.1% to about 5% of an oxidative compound.

7. A method according to claim 1 wherein said period for contacting said hair is between about 1 minute and 3 minutes.

8. A method according to claim 1 wherein said set time interval between each two consecutive such treatments is between about 1 day and about 3 days.

9. A method according to claim 1 wherein said hair has combing index in the range of 1.1 to 4.0.

10. A method according to claim 1 wherein said hair has combing force in the range of 5 to 55 gm force.

11. A method according to claim 1 wherein said hair has break stress in the range of 0.05 to 0.3 gm force/micron.

12. A method according to claim 1 wherein said composition delivers delta E of 0.1 to 65 on blonde hair and delta E of 0.1 to 8 on brown hair.

13. A method according to claim 1 wherein said hair has a ratio IR absorption at 1040 cm$^{-1}$/1240 cm$^{-1}$ in the range of 0.01 to 1.5.

14. A method according to claim 1 wherein said oxidative compound is selected from the group consisting of hydrogen peroxide, urea peroxide, melamine peroxide, sodium perborate and sodium percarbonate.

15. A method according to claim 1 wherein part ai comprises from about 35% to about 98.9% water.

16. A method according to claim 1, wherein the mixture of part ai and part aii has a neat viscosity of from about 500 cps to about 60,000 cps at 26.7 degrees C., as measured by a Brookfield RVTDCP with a spindle CP-41 at 1 RPM for 3 minutes.

17. A method for maintaining hair color through the use of a permanent hair dye which comprises subjecting said hair to successive treatments, having a set time interval between each two consecutive such treatments, wherein each treatment comprises:
  a.) contacting said hair for a period of about 5 seconds to about 3 minutes with a recently made mixture of:
    part ai: dye intermediates in water alkaline pH;
    part aii: oxidizing compound in water at acidic pH;
  b.) rinsing said mixture from said hair with water;
and wherein said number of treatments with an identically formulated mixture is between 6 and about 30; said set time interval between each two consecutive treatments is between about 8 hours and 30 days.

18. A method according to claim 1 wherein said dye intermediate in part ai is present at about 0.1% to about 1%.

19. A method according to claim 1 wherein said oxidizing compound in part aii is present at about 2% to about 5%.

20. A dispenser for dispensing simultaneously or nearly simultaneously part ai and part aii according to claim 1, which comprises:
  A.) a means for holding part ai and part aii in physically separate locations;
  B.) a means for protecting part ai and part aii from air prior to dispensing;
  C.) a means for dispensing part ai and part aii in equal amounts and in physical proximity to each other.

21. A method according to claim 1 wherein part ai and part aii are mixed by hand.

22. A method according to claim 1 which comprises rinsing said mixture of part ai and part aii from said hair with water in a shower.

* * * * *